US008838136B2

(12) United States Patent
Carnes et al.

(10) Patent No.: US 8,838,136 B2
(45) Date of Patent: Sep. 16, 2014

(54) SYSTEM, METHOD, AND SOFTWARE FOR CONFIGURING COMMUNICATION WITH MEDICAL DEVICES

(75) Inventors: Tony C. Carnes, Gainesville, FL (US); William A. Jordan, Westminister, CO (US)

(73) Assignee: Covidien LP, Mansfield, MA (US)

( * ) Notice: Subject to any disclaimer, the term of this patent is extended or adjusted under 35 U.S.C. 154(b) by 151 days.

(21) Appl. No.: 13/596,721

(22) Filed: Aug. 28, 2012

(65) Prior Publication Data
US 2014/0065952 A1    Mar. 6, 2014

(51) Int. Cl.
*H04W 24/00* (2009.01)
(52) U.S. Cl.
USPC .......... 455/456.1; 455/404.2; 455/426.2
(58) Field of Classification Search
USPC ........ 455/41.2, 41.3, 404.1, 404.2, 426.1, 455/426.2, 456.1, 456.2, 550.1, 561.1, 455/561.2
See application file for complete search history.

(56) References Cited

U.S. PATENT DOCUMENTS

| | | | |
|---|---|---|---|
| 7,650,146 B2 * | 1/2010 | Eberhart | 455/421 |
| 8,238,975 B2 * | 8/2012 | Vallapureddy et al. | 455/562.1 |
| 8,437,689 B2 * | 5/2013 | Mazar | 455/1 |
| 2004/0121767 A1 * | 6/2004 | Simpson et al. | 455/426.1 |
| 2008/0129465 A1 * | 6/2008 | Rao | 340/286.02 |

* cited by examiner

*Primary Examiner* — Nhan Le

(57) ABSTRACT

A method for configuring communication with medical devices includes a receiving, at a configuration interface, a first input indicative of first configuration parameters for a first medical device from a user and a second input indicative of second configuration parameters for a second medical device from the user. The first configuration parameters include at least one of a frequency parameter, a selection parameter, a compression parameter, an output parameter, and a port parameter. The method further includes receiving, at the configuration interface, first patient parameters from the first medical device and second patient parameters from the second medical device. The method further includes transmitting a first selected subset of the first patient parameters based on the first configuration parameters and transmitting a second selected subset of the second patient parameters based on the second configuration parameters.

20 Claims, 4 Drawing Sheets

SYSTEM, METHOD, AND SOFTWARE FOR CONFIGURING COMMUNICATION WITH MEDICAL DEVICES

TECHNICAL FIELD

The present disclosure relates generally to medical device management, and more particularly to a system, method, and software for configuring communication with medical devices.

BACKGROUND

Many medical devices support multiple output techniques. For example, certain medical devices may output data in a textual format while other medical devices may output data in binary format. Certain medical devices may have different rates of output for the output data.

SUMMARY

According to the present disclosure, disadvantages and problems associated with previous techniques for medical device management may be reduced or eliminated.

In certain embodiments, a method for configuring communication with medical devices includes receiving, at a configuration interface, a first input indicative of first configuration parameters for a first medical device from a user. The first configuration parameters include at least one of a frequency parameter, a selection parameter, a compression parameter, an output parameter, and a port parameter. The method further includes receiving, at the configuration interface, a second input indicative of second configuration parameters for a second medical device from the user. The method further includes receiving, at the configuration interface, first patient parameters from the first medical device. The method further includes receiving, at the configuration interface, second patient parameters from the second medical device. The method further includes transmitting a first selected subset of the first patient parameters based on the first configuration parameters. The method further includes transmitting a second selected subset of the second patient parameters based on the second configuration parameters.

Certain embodiments of the present disclosure may provide one or more technical advantages. Conventional medical devices output a fixed format of data to external systems. However, the amount of relevant output data desired by one external system may be far different from another external system. In addition, the transmission of potentially extraneous or redundant output data may lead to network congestion.

In certain embodiments of the present disclosure, a configuration interface is provided that allows end-users to customize patient parameters and other data that is transmitted from a patient parameter receiving device such as a data collection server described in more detail below. Thus, at least one technical advantage of this disclosure includes a reduction in network traffic and parsing overhead at a receiving system by selecting a subset of patient parameters and other data to be transmitted instead of all available patient parameters and other data. Another technical advantage of this disclosure includes a capacity to extend a single serial port to multiple ports with different protocols per port to allow different systems to communicate with a medical device in different ways. In certain embodiments of the disclosure, a user may implement the configuration interface to specify: (1) a selection parameter that indicates the desired patient parameters to be parsed and passed on by the configuration interface; (2) a frequency parameter that indicates the frequency at which the data should be captured and passed (e.g., switching between any of a number of baud rates such as 2400, 4800, 9600, 14400, 28800, and 57600 baud rates or the frequency parameter may be throttled up or down to transmit patient parameters (or a subset of patient parameters) depending on system needs); (3) a compression parameter that indicates certain outputs from a medical device to be captured, compressed, and transmitted together to a receiving system at a specified interval; (4) an output parameter that indicates a selection of one of several output protocols for transmitting the data to a receiving system; and (5) a port parameter that indicates which forwarding port is associated with which output protocol.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DESCRIPTION OF EXAMPLE EMBODIMENTS

Figure 1:
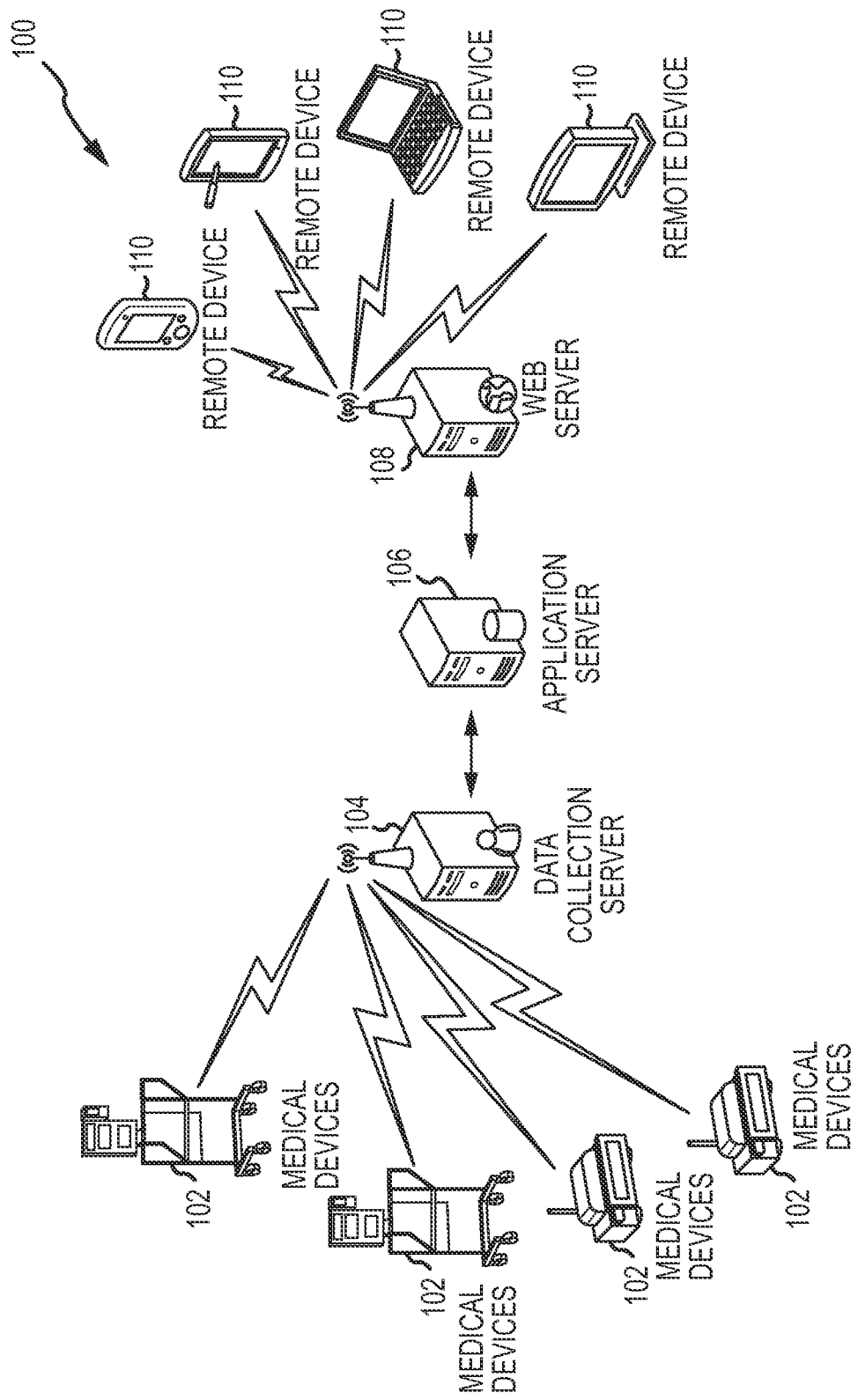
FIG. 1 illustrates an example system for configuring communication with medical devices, according to certain embodiments of the present disclosure.

FIG. 1 illustrates an example system 100 for configuring communication with medical devices, according to certain embodiments of the present disclosure. System 100 includes one or more medical devices 102, a data collection server 104, an application server 106, a web server 108, and one or more remote devices 110. According to one embodiment, system 100 is operable to monitor medical devices 102 and transform patient parameters into display parameters. In certain embodiments, medical devices 102 generate patient parameters or store patient parameters input by a user, such as a clinician. Patient parameters may refer to any patient identifiers, medical history, clinician notes, alarm thresholds, alarm events, device settings, measurements of values indicating physiological conditions such as oxygen saturation levels, pulse rates, heart rates, other vital signs, and any other output data from medical devices 102. Each medical device 102 may be connected to data collection server 104, which stores the patient parameters in a database. Application server 106 retrieves the patient parameters from the database and processes the patient parameters into display parameters for web server 108. Remote devices 110 request and receive the display parameters and display the display parameters through a browser, thereby enabling clinicians using the remote devices 110 to view the display parameters in remote locations. As described in more detail below, a configuration interface at data collection server 104 includes logic that may receive, parse, interpret, and translate patient parameters received from different medical devices 102.

Although this particular implementation of system 100 is illustrated and primarily described, the present disclosure contemplates any suitable implementation of system 100 according to particular needs. For example, although this implementation of the configuration interface is illustrated with remote devices 110 that may be using a web interface or a client/server interface, this disclosure contemplates any suitable implementation of the configuration interface. In addition, a component of system 100 may include any suitable arrangement of elements, for example, an interface, logic, memory, other suitable element, or a combination of any of the preceding. An interface receives input, sends output, processes the input and/or output, performs other suitable operation, or performs a combination of any of the preceding. An interface may comprise hardware and/or software.

System 100 may include one or more medical devices 102. Medical devices 102 may be any devices that are used for tracking or treating patients. For example, medical devices 102 may include a ventilator connected to a patient to deliver respiratory therapy. As another example, medical devices 102 may include a pulse oximeter that monitors the oxygen saturation of a patient's blood. As another example, medical devices 102 may include a device for tracking a patient without monitoring physiological conditions. In short, medical devices 102 may include any suitable combination of software, firmware, and hardware used to support any medical function. It should be noted that any suitable number of medical devices 102 may be included in system 100. In addition, there may be multiple groups of medical devices 102 in system 100.

According to one embodiment, in addition to performing a medical function, medical devices 102 may generate output data tracked by medical devices 102. For example, the ventilator may generate entries indicating the average volume of air expelled in each breath. The ventilator may generate entries including the parameter settings used by the ventilator and an identification of whether any alarms have been triggered. The ventilator may store the generated entries in local memory and output the entries. In some embodiments, medical devices 102 may generate output data that is related to tracking patient identifications or locations, without necessarily generating data related to a physiological condition. In certain embodiments, medical devices 102 may output data in response to a data request. In certain other embodiments, medical devices 102 may constantly stream output data.

Medical devices 102 may be communicatively coupled to data collection server 104 via a network, according to one embodiment. The network facilitates wireless or wireline communication. The network may communicate, for example, IP packets, Frame Relay frames, Asynchronous Transfer Mode (ATM) cells, voice, video, data, and other suitable information between network addresses. The network may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, medical devices may be communicatively coupled to other suitable devices including data collection server 104, application server 106, web server 108, and remote devices 110.

System 100 may include one or more data collection servers 104, referred to primarily in the singular throughout this disclosure. Data collection server 104 may include one or more electronic computing devices operable to receive, transmit, process, and store data associated with system 100. For example, data collection server 104 may include one or more general-purpose PCs, Macintoshes, workstations, Unix-based computers, server computers, one or more server pools, or any other suitable devices. In certain embodiments, data collection server 104 includes a web server. In short, data collection server 104 may include any suitable combination of software, firmware, and hardware. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

According to one embodiment, data collection server 104 receives patient parameters from medical devices 102. For example, data collection server 104 may request patient parameters from a medical device 102 and receives patient parameter sets from the medical device 102 in response to the request. As another example, data collection server 104 may receive streamed output data from a medical device 102. As another example, data collection server 104 may be configured to periodically request new data from medical device 102. Data collection server 104 may map the received patient parameters to match internal fields in the database and then transmit the data to a database, according to one embodiment. The stored data may be accessed by application server 106.

System 100 may include one or more application servers 106, referred to primarily in the singular throughout this disclosure. Application server 106 may include one or more electronic computing devices operable to receive, transmit, process, and store data associated with system 100. For example, application server 106 may include one or more general-purpose PCs, Macintoshes, workstations, Unix-based computers, server computers, one or more server pools, or any other suitable devices. In short, application server 106 may include any suitable combination of software, firmware, and hardware. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 creates a data service that runs on a conventional web services platform for transmitting data to web server 108. For example, application server 106 may create webpage data using the patient parameters, and that webpage data is transmitted to web server 108 for display. Application server 106 may maintain an activity log that logs data requests from remote devices 110 to track certain activities performed at the remote devices 110. Therefore, if a clinician selects a particular patient representation to zoom in and view ventilator data specific to that patient, that selection may trigger a data request that is logged by application server 106. When creating the webpage data, application server 106 may compare the current parameter settings of the ventilator, as indicated by entries in the patient parameter set, to prior parameter settings. If any changes are detected, application server 106 may flag those changes for presentation to users on remote devices 110. Specifically, application server 106 may create data causing the depiction of the changed patient parameters on the remote devices 110 to change color. Application server 106 may create additional data that causes a pop-up window to appear on the mobile device when any of the changed patient parameters are selected. That window may list all of the changed patient parameters and provides a single button through which a user may indicate that that the changed patient parameters have been viewed. If that button is activated, the mobile device may transmit a message to application server 106 and application server 106 may then unflag those patient parameters, such that the depiction of those patient parameters on remote device 110 may return to the original color. In certain embodiments, application server 106 may transmit data directly to remote devices 110.

System 100 may include one or more web servers 108, referred to primarily in the singular throughout this disclosure. Web server 108 may include one or more electronic computing devices operable to receive, transmit, process, and store data associated with system 100. For example, web server 108 may include one or more general-purpose PCs, Macintoshes, workstations, Unix-based computers, server computers, one or more server pools, or any other suitable devices. In short, web server 108 may include any suitable combination of software, firmware, and hardware. Although a single web server 108 is illustrated, the present disclosure contemplates system 100 including any suitable number of web servers 108. Moreover, although referred to as a web server, the present disclosure contemplates web server 108 comprising any suitable type of processing device or devices.

According to one embodiment, web server 108 creates a data service that runs on a conventional web services platform for receiving data from application server 106 and transmitting data to remote devices 110. For example, web server 108 may receive webpage data from application server 106 and transmitted, upon request in certain embodiments, to remote devices 110.

System 100 may include one or more remote devices 110. Remote devices 110 may be any device that provides output to and can receive input from a user, such as a clinician. Each remote device 110 may include one or more computer systems at one or more locations. Each computer system may include any appropriate input devices (such as a keypad, touch screen, mouse, or other device that can accept input), output devices, mass storage media, or other suitable components for receiving, processing, storing, and communicating data. Both the input device and output device may include fixed or removable storage media such as a magnetic computer disk, CD-ROM, or other suitable media to both receive input from and provide output to a user. Each computer system may include a personal computer, workstation, network computer, kiosk, wireless data port, personal data assistant (PDA), one or more processors within these or other devices, or any other suitable processing device.

According to one embodiment, remote devices 110 display one or more web pages hosted by application server 106 and/or web server 108 with patient parameters from medical devices 102. For example, a clinician may activate a browser on remote device 110 and navigate to the web page hosted by web server 108. The browser may render the web page, which includes patient parameters generated by medical devices 102. The web page may provide a summary of all the medical devices 102 under a clinician's responsibility. In addition, the web may display a detailed view that displays specific device data, therapy parameter data, and alarm status data.

Although FIG. 1 depicts separate devices for data collection server 104, application server 106, and web server 108, it will be readily apparent that the functions of these devices may be combined into a single device that receives patient parameters from medical devices 102 and transforms the patient parameters into display parameters. It will also be understood that this single device may alternatively transmit the display parameters to remote device 110. In certain embodiments, data collection server 104 may be a bedside device that receives patient parameters from medical devices 102.

It will also be understood that the functions may be allocated differently than shown, with application server 106 additionally performing the functions of web server 108 or the functions of data collection server 104. In another embodiment, a single device may receive patient parameters, transform those patient parameters into display parameters, and display the display parameters on a screen.

A user of system 100 may connect many different types of medical devices 102 to examine a combination of patient parameters. Each medical device 102 may output a fixed format of data to data collection server 104. In certain embodiments, there may be a certain amount and type of relevant output data from a particular medical device for some systems and a different amount and type of relevant output data from for other systems. In addition, there may be additional issues with communicating large amounts of information from medical devices 102 to multiple data collection servers 104 across a network including network bandwidth issues and end-system consumption issues.

In certain embodiments of the disclosure, system 100 may include a configuration interface to address these concerns. The configuration interface may refer to any suitable hardware and/or software operable to be configured to filter patient parameters received from different medical devices 102 at data collection server 104. Filtering patient parameters may refer to specifying a certain subset of patient parameters to be transmitted by data collection server 104 based on configuration parameters such as a selection parameter that indicates the desired patient parameters to be parsed and passed on by the configuration interface, a frequency parameter that indicates the frequency at which the data should be captured and passed (e.g., switching from a 9600 baud rate to a 14400 baud rate), a compression parameter that indicates certain outputs from a medical device to be captured, compressed, and transmitted together in a subset at a specified interval, an output parameter that indicates a selection of one of several output protocols for transmitting the data to a receiving system, a port parameter that indicates which forwarding port is associated with which output protocol. Therefore, the configuration interface may reduce network traffic, reduce parsing overhead, and ensure that desired information is transmitted instead of all available information. Additional details of example embodiments of the configuration interface are discussed below with reference to FIGS. 2-4.

Figure 2:
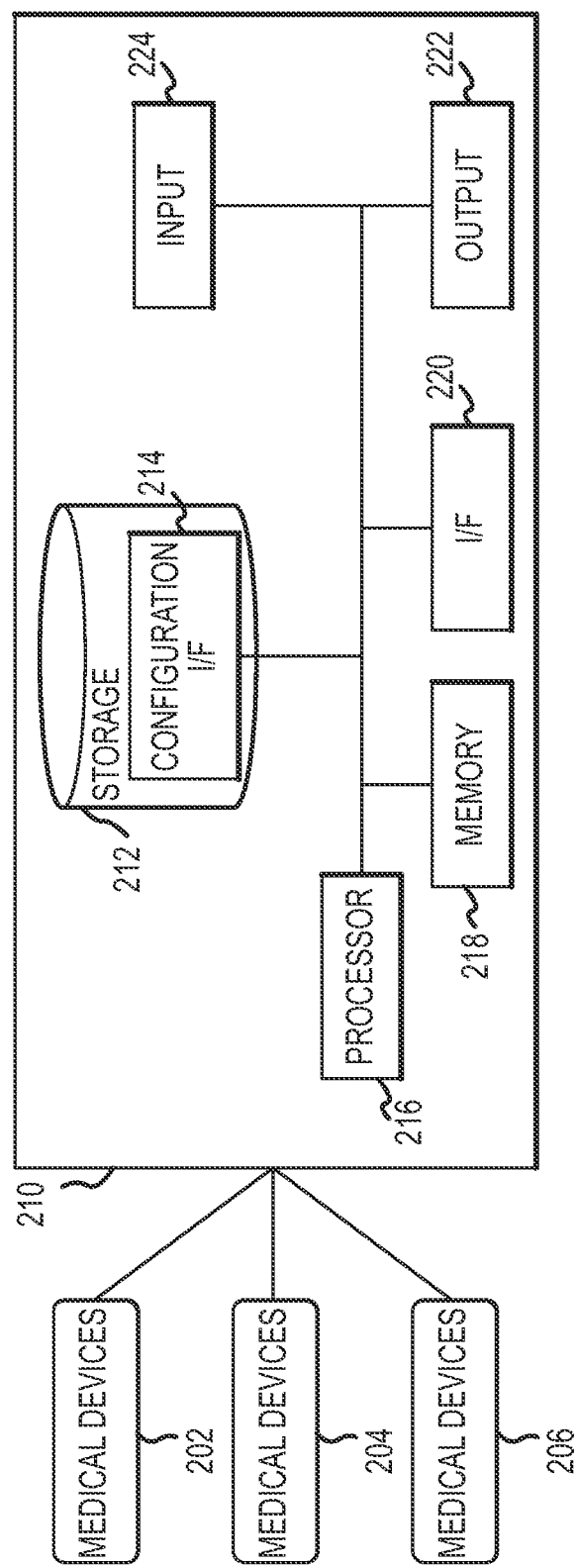
FIG. 2 illustrates an example data collection server of the system for configuring communication with medical devices in FIG. 1, according to certain embodiments of the present disclosure.

FIG. 2 illustrates an example data collection server 210 of the system 100 for configuring communication with medical devices in FIG. 1, according to certain embodiments of the present disclosure. Data collection server 210 may be substantially similar to data collection server 104 of FIG. 1. In FIG. 2, a data collection server 210 is shown as a server communicatively coupled with a medical device 202, a medical device 204, and a medical device 206. Medical devices 202-206 may be substantially similar to medical devices 102 of FIG. 1. Data collection server 210 includes a storage device 212, a configuration interface 214, a processor 216, a memory 218, a communication interface (I/F) 220, an output device 222, and an input device 224, which are discussed in further detail below. Although this particular implementation of data collection server 210 is illustrated and primarily described, the present disclosure contemplates any suitable implementation of data collection server 210 according to particular needs.

Storage device 212 may include any suitable device operable for storing data and instructions. Storage device 212 may include, for example, a magnetic disk, flash memory, optical disk, or other suitable data storage device.

Configuration interface 214 may include any suitable logic embodied in computer-readable media, and when executed, that is operable to be configured to filter patient parameters received from different medical devices 102. For example, configuration interface 214 may include logic for receiving a first input indicative of first configuration parameters for a first medical device from a user and a second input indicative of second configuration parameters for a second medical device from the user. The first configuration parameters may include at least one of a frequency parameter, a selection parameter, a compression parameter, an output parameter, and a port parameter. The configuration interface 214 may receive first patient parameters from the first medical device and second patient parameters from the second medical device. The configuration interface 214 may transmit a first selected subset of the first patient parameters based on the first configuration parameters and transmit a second selected subset of the second patient parameters based on the second configuration parameters. Additional details of configuration interface 214 and configuration parameters are provided below with reference to FIG. 3.

Processor 216 may include any suitable device operable to execute instructions and manipulate data to perform operations for configuration interface 214. Processor 216 may include, for example, any type of central processing unit (CPU).

Memory 218 may include any computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server). Memory 218 may comprise any other computer-readable tangible medium, or a combination of any of the preceding.

I/F 220 may include any suitable device operable to receive input for configuration interface 214, send output from configuration interface 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a LAN, WAN, or other communication system that allows configuration interface 214 to communicate to other devices. I/F 220 may include one or more ports, conversion software, or a combination of any of the preceding.

Output device 222 may include any suitable device operable for displaying information to a user. Output device 222 may include, for example, a video display, a printer, a plotter, or other suitable output device. In certain embodiments, output device 222 may reformat data in any suitable format to be transmitted to other systems.

Input device 224 may include any suitable device operable to input, select, and/or manipulate various data and information. Input device 224 may include, for example, a keyboard, mouse, graphics tablet, joystick, light pen, microphone, scanner, or other suitable input device.

Modifications, additions, or omissions may be made to data collection server 210 without departing from the scope of the disclosure. The components of data collection server 210 may be integrated or separated. Moreover, the operations of data collection server 210 may be performed by more, fewer, or other components.

For example, although configuration interface 214 is displayed as part of storage device 212, configuration interface 214 may be stored in any suitable location, including in another suitable device shown in FIG. 1, and the operations of configuration interface 214 may be performed by more than one component. Additionally, operations of data collection server 210 may be performed using any suitable logic. As used in this document, "each" refers to each member of a set or each member of a subset of a set. Further details of an example data collection server 210 and the operations of configuration interface 214 are provided below with reference to FIG. 3.

Figure 3:
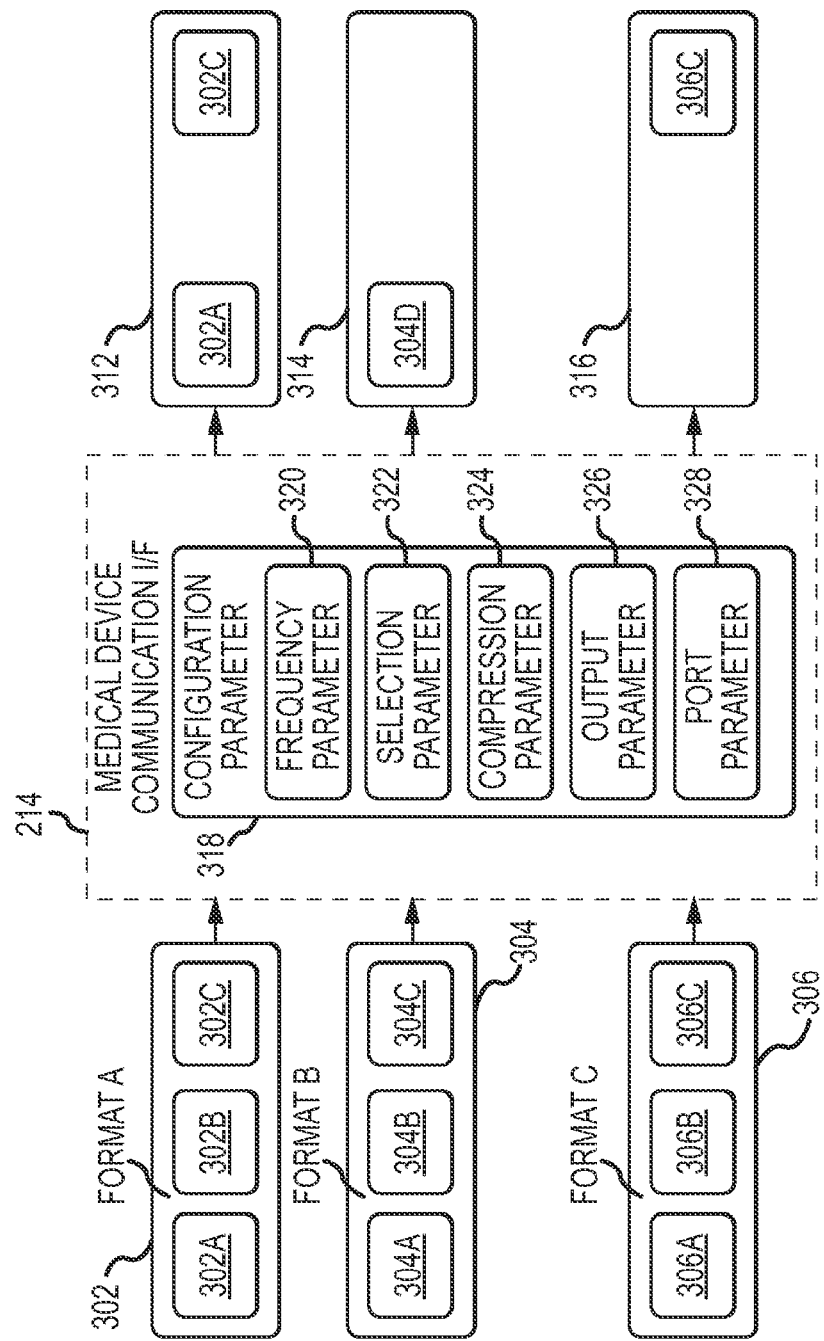
FIG. 3 illustrates one embodiment of an example operation of configuration interface of FIG. 2, according to certain embodiments of the present disclosure.

FIG. 3 illustrates one embodiment of an example operation of configuration interface 214 of FIG. 2, according to certain embodiments of the present disclosure. The illustrated embodiment includes a format 302, a format 304, and a format 306 and associated patient parameters, such as patient parameters 302A, 302B, and 302C in format 302, which may be generated by respective medical devices, such as medical devices 102 in FIG. 1. A format may refer to any systematic arrangement of patient parameters and may include any of a data speed, data type, data count, data encoding, data syntax, data format, or any combination thereof. In certain embodiments, each of formats 302-306 may represent a particular proprietary format for medical devices 102. For example, format 302 may be associated with patient parameters output from a first medical device 102 in FIG. 1 and format 304 may be associated with a second medical device 102 in FIG. 1.

According to certain embodiments of the disclosure, formats 302-306 and their associated patient parameters may be filtered at configuration interface 214 to specify, for example: certain desired parameters to be parsed and transmitted, a frequency at which the data should be captured and transmitted, a compression factor to allow for multiple outputs from the medical device to be captured, compressed, and transmitted together at a specified interval, a selection of one of several output protocols for transmission, and a forwarding port associated with a certain output protocol. For example, in the illustrated embodiment, patient parameters 302A, 302B, and 302C and format 302 may be filtered to identify a subset of patient parameters to be parsed and transmitted, such as patient parameters 302A and 302C in format 312. As another example, in the illustrated embodiment, patient parameters 304A, 304B, and 304C in format 304 may be filtered by compressing patient parameters 302A, 302B, and 302C into a subset of patient parameters such as patient parameter 304D in format 314 that includes patient parameters 304A, 304B, and 304C in a compressed format. As another example, in the illustrated embodiment, configuration interface 214 may forward patient parameter 304A in format 314 to a particular output port and may forward patient parameters 302A and 302C in format 312 to a different output port.

In certain embodiments, configuration interface 214 may include certain configuration parameters, or modifications to configuration parameters, to filter patient parameters and the configuration parameters may be configured by a user. For example, in certain embodiments of the disclosure, a user may implement configuration interface 214 to specify a selection parameter that indicates the desired patient parameters to be parsed and passed on by configuration interface 214. As another example, in certain embodiments of the disclosure, a user may implement configuration interface 214 to specify a frequency parameter that indicates the frequency at which the data should be captured and passed (e.g., switching from a 9600 baud rate to a 14400 baud rate). In certain other embodiments, the frequency parameter may indicate a particular frequency, rate, or time period to receive and transmit (possibly filtered) data. For example, configuration interface 214 may forward patient parameters (or a subset of patient parameters) every second. However, certain receiving systems may not need data every second and, therefore, the frequency parameter may be throttled down to transmit patient parameters (or a subset of patient parameters) every minute, as an example. As another example, the frequency parameter may be throttled up depending on system needs. As another example, in certain embodiments of the disclosure, a user may implement configuration interface 214 to specify a compression parameter that indicates certain outputs from a medical device to be captured, compressed, and transmitted together to a receiving system at a specified interval. In certain embodiments, the compression parameter may facilitate capturing data at higher frequencies, and compress desired parameters, discarding others, and transmitting the compressed parameters out at desired intervals, making better use of network bandwidth. As another example, in certain embodiments of the disclosure, a user may implement configuration interface 214 to specify an output parameter that indicates a selection of one of several output protocols for transmitting the data to a receiving system. In certain embodiments, the baud rate described above may be specified in the output parameter. As another example, in certain embodiments of the disclosure, a user may implement configuration interface 214 to specify a port parameter that indicates which forwarding port is associated with which output protocol.

According to one embodiment, configuration interface 214 allows end-users to customize patient parameters and other data that is transmitted from a patient parameter receiving device such as data collection server 104. This may result in a reduction in network traffic and parsing overhead at data collection server 104 and/or application server 106 by selecting a subset of patient parameters and other data to be transmitted. In addition, another technical advantage of this disclosure includes a configuration interface 214 in data collection server 104 may allow data collection server 104 to extend a single serial port at a particular medical device 102 to multiple ports with different protocols per port to allow different systems, such as multiple application servers 106, to receive data and communicate with medical device 102 in different ways.

Figure 4:
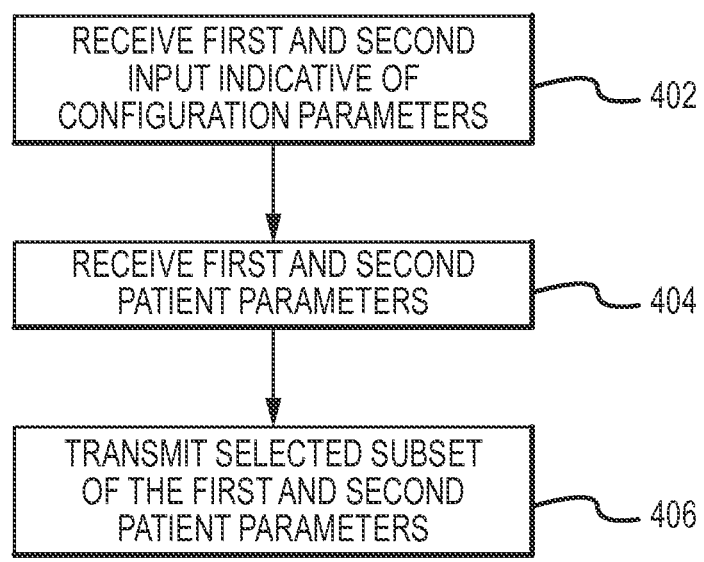
FIG. 4 illustrates an example method for configuring communication with medical devices, according to certain embodiments of the present disclosure.

FIG. 4 illustrates an example method for configuring communication with medical devices, according to certain embodiments of the present disclosure. The method begins at step 402 where first configuration parameters for a first medical device from a user and a second input indicative of second configuration parameters for a second medical device from the user are received. The first configuration parameters include at least one of a frequency parameter, a selection parameter, a compression parameter, an output parameter, and a port parameter. At step 404, first patient parameters from the first medical device and second patient parameters from the second medical device are received. At step 406, a first selected subset of the first patient parameters based on the first configuration parameters and a second selected subset of the second patient parameters based on the second configuration parameters are transmitted. It should be understood that some of the steps illustrated in FIG. 4 may be combined, modified or deleted where appropriate, and additional steps may be added to the flowchart. Additionally, as indicated above, steps may be performed in any suitable order without departing from the scope of the disclosure.

Although the present disclosure has been described with several embodiments, diverse changes, substitutions, variations, alterations, and modifications may be suggested to one skilled in the art, and it is intended that the disclosure encompass all such changes, substitutions, variations, alterations, and modifications as fall within the spirit and scope of the appended claims.

What is claimed is:

1. A method for configuring communication with medical devices, comprising:
   receiving, at a configuration interface, a first input indicative of a first plurality of configuration parameters for a first medical device from a user, the first plurality of configuration parameters comprising at least one of a frequency parameter, a selection parameter, a compression parameter, an output parameter, and a port parameter;
   receiving, at the configuration interface, a second input indicative of a second plurality of configuration parameters for a second medical device from the user;
   receiving, at the configuration interface, a first plurality of patient parameters from the first medical device;
   receiving, at the configuration interface, a second plurality of patient parameters from the second medical device;
   transmitting a first selected subset of the first plurality of patient parameters based on the first plurality of configuration parameters; and
   transmitting a second selected subset of the second plurality of patient parameters based on the second plurality of configuration parameters.

2. The method of claim 1, wherein the first input indicative of the first plurality of configuration parameters comprises a modification of the frequency parameter to throttle down transmission of patient parameters.

3. The method of claim 1, wherein the first input indicative of the first plurality of configuration parameters comprises a modification of the selection parameter to select certain patient parameters for transmission.

4. The method of claim 1, wherein the first input indicative of the first plurality of configuration parameters comprises a modification of the compression parameter to select multiple outputs from the first medical device to compress and transmit.

5. The method of claim 1, wherein the first input indicative of the first plurality of configuration parameters comprises a modification of the output parameter to select one of a plurality of output protocols for transmission of the first plurality of patient parameters.

6. The method of claim 1, wherein the first input indicative of the first plurality of configuration parameters comprises a modification of the port parameter to a particular forwarding port associated with a particular output protocol.

7. The method of claim 1, further comprising:
   receiving, at the configuration interface, a third input indicative of a third plurality of configuration parameters for a third medical device from the user;
   receiving, at the configuration interface, a third plurality of patient parameters from the third medical device; and
   transmitting a third selected subset of the third plurality of patient parameters based on the third plurality of configuration parameters.

8. A system for configuring communication with medical devices, comprising:
   one or more processing units operable to:
   receive, at a configuration interface, a first input indicative of a first plurality of configuration parameters for a first medical device from a user, the first plurality of configuration parameters comprising at least one of a frequency parameter, a selection parameter, a compression parameter, an output parameter, and a port parameter;

receive, at the configuration interface, a second input indicative of a second plurality of configuration parameters for a second medical device from the user;

receive, at the configuration interface, a first plurality of patient parameters from the first medical device;

receive, at the configuration interface, a second plurality of patient parameters from the second medical device;

transmit a first selected subset of the first plurality of patient parameters based on the first plurality of configuration parameters; and transmit a second selected subset of the second plurality of patient parameters based on the second plurality of configuration parameters.

9. The system of claim 8, wherein the first input indicative of the first plurality of configuration parameters comprises a modification of the frequency parameter to throttle down transmission of patient parameters.

10. The system of claim 8, wherein the first input indicative of the first plurality of configuration parameters comprises a modification of the selection parameter to select certain patient parameters for transmission.

11. The system of claim 8, wherein the first input indicative of the first plurality of configuration parameters comprises a modification of the compression parameter to select multiple outputs from the first medical device to compress and transmit.

12. The system of claim 8, wherein the first input indicative of the first plurality of configuration parameters comprises a modification of the output parameter to select one of a plurality of output protocols for transmission of the first plurality of patient parameters.

13. The system of claim 8, wherein the first input indicative of the first plurality of configuration parameters comprises a modification of the port parameter to a particular forwarding port associated with a particular output protocol.

14. The system of claim 8, wherein the one or more processing units are further operable to:

receive, at the configuration interface, a third input indicative of a third plurality of configuration parameters for a third medical device from the user;

receive, at the configuration interface, a third plurality of patient parameters from the third medical device; and transmit a third selected subset of the third plurality of patient parameters based on the third plurality of configuration parameters.

15. Software for configuring communication with medical devices, the software embodied in a computer-readable medium and when executed operable to:

receive, at a configuration interface, a first input indicative of a first plurality of configuration parameters for a first medical device from a user, the first plurality of configuration parameters comprising at least one of a frequency parameter, a selection parameter, a compression parameter, an output parameter, and a port parameter;

receive, at the configuration interface, a second input indicative of a second plurality of configuration parameters for a second medical device from the user;

receive, at the configuration interface, a first plurality of patient parameters from the first medical device;

receive, at the configuration interface, a second plurality of patient parameters from the second medical device;

transmit a first selected subset of the first plurality of patient parameters based on the first plurality of configuration parameters; and transmit a second selected subset of the second plurality of patient parameters based on the second plurality of configuration parameters.

16. The software of claim 15, wherein the first input indicative of the first plurality of configuration parameters comprises a modification of the frequency parameter to throttle down transmission of patient parameters.

17. The software of claim 15, wherein the first input indicative of the first plurality of configuration parameters comprises a modification of the selection parameter to select certain patient parameters for transmission.

18. The software of claim 15, wherein the first input indicative of the first plurality of configuration parameters comprises a modification of the compression parameter to select multiple outputs from the first medical device to compress and transmit.

19. The software of claim 15, wherein the first input indicative of the first plurality of configuration parameters comprises a modification of the output parameter to select one of a plurality of output protocols for transmission of the first plurality of patient parameters.

20. The software of claim 15, wherein the software is further operable to:

receive, at the configuration interface, a third input indicative of a third plurality of configuration parameters for a third medical device from the user;

receive, at the configuration interface, a third plurality of patient parameters from the third medical device; and transmit a third selected subset of the third plurality of patient parameters based on the third plurality of configuration parameters.

* * * * *